(12) United States Patent
Forbes (10) Patent No.: US 9,427,487 B1
(45) Date of Patent: Aug. 30, 2016

(54) ATTACHABLE FABRIC SCENT DIFFUSER

(71) Applicant: Lou Ann Forbes, Maple Park, IL (US)

(72) Inventor: Lou Ann Forbes, Maple Park, IL (US)

(*) Notice: Subject to any disclaimer, the term of this patent is extended or adjusted under 35 U.S.C. 154(b) by 0 days.

(21) Appl. No.: 14/488,226

(22) Filed: Sep. 16, 2014

(51) Int. Cl.
*A61L 9/12* (2006.01)
*A01K 27/00* (2006.01)

(52) U.S. Cl.
CPC .............. *A61L 9/12* (2013.01); *A01K 27/001* (2013.01)

(58) Field of Classification Search
CPC ...... A61L 9/12; A61L 9/127; A01M 31/008; A01K 27/001; A01K 27/007; A01K 27/008
See application file for complete search history.

(56) References Cited

U.S. PATENT DOCUMENTS

| 4,465,232 | A | * | 8/1984 | Field | 239/36 |
| 4,722,477 | A | * | 2/1988 | Floyd | 239/36 |
| 2012/0315317 | A1 | * | 12/2012 | O'Hara | A01N 25/08 424/414 |

* cited by examiner

*Primary Examiner* — Darren W Gorman
(74) *Attorney, Agent, or Firm* — Law Offices of Steven W. Weinrieb (57) ABSTRACT

A fabric scent diffuser that can be easily and strongly attached to a pet collar which is then worn by a pet with the portable scent diffuser providing an effective scent or vapor to the pet, yet can be removed when desired. The fabric scent diffuser has a fabric strap, absorbent material such as cotton to which a scent oil or solution is applied, and has a fabric cover over the absorbent material, all stitched together to hold the absorbent material and fabric cover in place on the fabric strap. Hook and loop fastener material are attached near the ends of the strap so that the fabric scent diffuser can be looped around a pet collar and secured with the hook and loop material. A kit with additional components, and methods of fabrication and use, are provided.

15 Claims, 7 Drawing Sheets

ATTACHABLE FABRIC SCENT DIFFUSER

CROSS REFERENCES TO RELATED APPLICATIONS

None.

BACKGROUND OF THE INVENTION

1. Field of the Invention

The present invention pertains to apparatus and methods for a releasably attachable vapor delivery device, and more particularly for a portable reservoir and delivery device for scents, oils, solutions, and the like, attachable to pet collars.

2. Description of the Prior Art

Prior art approaches include spraying scents or solutions into a room, directly onto an animal or clothing, or in a particular region where activity of such solutions is desired. Other approaches include candle-based, light-bulb attached, plug-in or other types of heated diffuser to evaporate a solution, melt a wax or oil, or otherwise give off desired vapors or scents. For example, various sorts of delivery approaches are used for room fresheners, bug repellents, fragrances, calming vapors, or other beneficial substances that can act on a body to calm, repel, or otherwise modify behavior, provide aromatherapy, or just to be pleasing to one in the vicinity of the vapor or scent.

It can be beneficial to modify the behavior of pets such as dogs, for example, using scents, vapors of essential oils or solutions, hormones, pheromones, insect repellents, and so forth, to apply them to a collar, mount them in a location near the pet, or apply them directly to the pet. Some substances, however, are best not applied in direct contact with the animal, but are best delivered as a vapor so that they may be inhaled or absorbed through the nose or mouth. The vapor can provide a calming or soothing effect, affect alertness or stress, or reinforce behavior, for example.

In one approach by England, illustrated by U.S. Pat. No. D619,695, a scent diffuser is attached to a strap which is used to hold the scent diffuser on a pet collar; the strap passes around the collar and the two ends of the strap have snap components which snap together to secure the strap on the collar and hold the scent diffuser in place. This approach has multiple problems which have as yet not been overcome. In one aspect, the diffuser reservoir can hold sufficient oil or solution, but the access hole available for diffusion or transmission of vapor is quite small. While some substances may be adequately delivered over a long time through such a small access hole, many substances require a larger area to deliver an effective amount or concentration of vapor. For example, some substances can provide calming or other behavior modification and are quite useful when needed for a particular event which may be short in duration, such as a visit to the veterinarian, a walk, visit of strangers or unfamiliar animals, or other stressful situations. In these cases, a relatively short duration of exposure is needed, but a relatively higher concentration or amount of diffused vapor may be required to be effective. The approach of England, for example, provides a more limited concentration of vapor, being limited by the small access hole size.

Another issue for prior approaches such as that of England, is that small snaps such as would be useable on a collar-attachable scent diffuser device are known to be unreliable attachment mechanisms, with particularly certain breeds and certain dispositions of animals very likely to scratch repeatedly in a way which dislodges or unsnaps the snapped fastener. Once dislodged, the scent diffuser can be a hazard for the animal, presenting health risks if the scent diffuser is ingested, for example. Also, a dislodged scent diffuser could simply get lost.

Still another issue for prior approaches is that the plastic reservoir with small access hole can be difficult to clean, such as to remove contaminants, or when changing to a different oil or solution.

Yet another issue for prior approaches is that a thick diffuser such as that of England, would be more easily caught by the animal during scratching, and therefore more easily dislodged. Further, the rigid reservoir would have sharp edges and may crack under abuse by the animal, especially if it were dislodged, presenting further health risks to the animal.

There is continued need for improved devices and methods for scent diffusers which are attachable to pet collars or other equipment. There is particular need for a scent diffuser which provides improved diffusion rates or scent concentrations for improved effectiveness. Also, there is particular need for a scent diffuser with more robust attachment to a pet collar, yet is attached and detached easily when desired.

SUMMARY OF THE INVENTION

The general purpose of the present invention is to provide a portable scent diffuser which can be easily and strongly attached to a pet collar which is then worn by a pet with the portable scent diffuser providing an effective scent or vapor when desired.

According to one embodiment of the present invention, there is provided a fabric scent diffuser which is removably attachable to a pet collar.

According to another embodiment of the present invention, there is provided a kit for delivery of scents or vapor to a body, including a fabric scent diffuser which can removably attached to a pet collar, and oil or solution to place into the fabric scent diffuser and provide the substance which is diffused as a scent or vapor.

According to yet another embodiment of the present invention, there is provided a kit for delivery of scents or vapor to a body, including a fabric scent diffuser which can removably attached to a pet collar, oil or solution to place into the fabric scent diffuser and provide the substance which is diffused as a scent or vapor, and a sealable storage container to minimize loss of vapor from the fabric scent diffuser when in storage.

According to still another embodiment of the present invention, there is provided a method for temporary delivery of scents or vapor to a body, including providing a fabric scent diffuser which can removably attached to a pet collar, providing an oil or solution to place into the fabric scent diffuser, attaching the fabric scent diffuser to a pet collar, using the fabric scent diffuser to deliver scents or vapor to be absorbed or inhaled, and removing the fabric scent diffuser from the pet collar.

According to a further embodiment of the present invention, there is provided a method for fabricating a fabric scent diffuser, including providing a fabric strap, absorbent, a fabric cover, stitching, and hook and loop fastener; sewing around most of the fabric cover attach the fabric cover to the central portion of the fabric strap and forming a pocket; filling the pocket with absorbent; sewing around the remainder of the fabric cover to secure the fabric cover and absorbent in place; and sewing the hook and loop fastener to opposite sides of the strap near opposite ends of the strap.

One significant aspect and feature of the present invention is a scent diffuser made of fabric.

Another significant aspect and feature of the present invention is a scent diffuser which is easily attached to a pet collar and removed by a user, but will not be easily removed by the animal.

Yet another significant aspect and feature of the present invention is a scent diffuser with a large access area for diffusion of scent.

Still another significant aspect and feature of the present invention is a scent diffuser which can easily be cleaned.

A further significant aspect and feature of the present invention is a scent diffuser which can be easily manufactured.

A still further significant aspect and feature of the present invention is a kit including a scent diffuser made of fabric, a sealable container of scent oil or solution, and a sealable storage container to protect the scent diffuser and slow the drying out of the scent oil or solution from the scent diffuser.

Having thus briefly described one or more embodiments of the present invention, and having mentioned some significant aspects and features of the present invention, it is the principal object of the present invention to provide convenient means of temporary delivery of a scent to a pet for inhalation or absorption through the nose or mouth.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, which are not to scale, in which like reference numerals designate like parts throughout the figures thereof and wherein.

DETAILED DESCRIPTION OF THE PREFERRED EMBODIMENTS

Figure 1A:
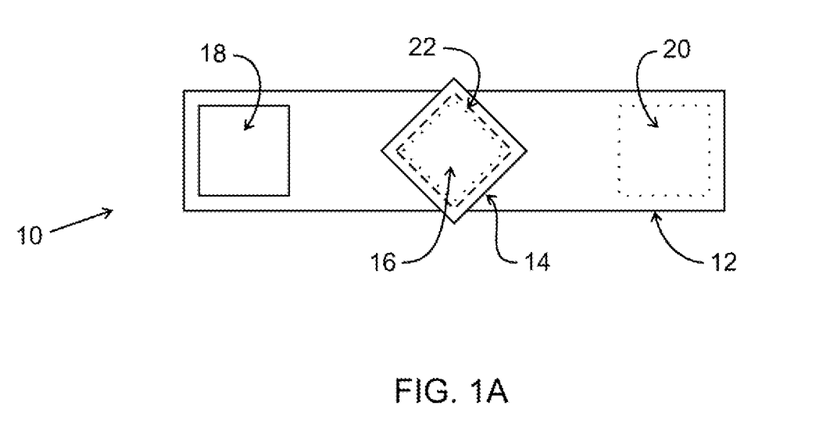
FIG. 1A is a face view of an example fabric scent diffuser according to the present invention.
Figure 1B:
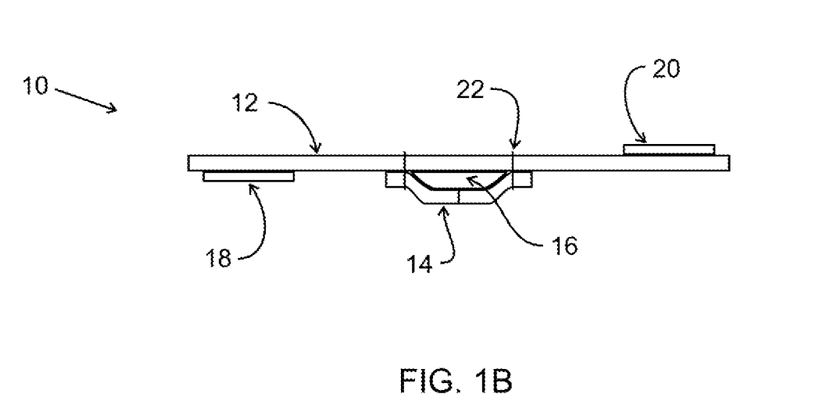
FIG. 1B is an edge view of the fabric scent diffuser of FIG. 1A.

FIG. 1A illustrates an example fabric scent diffuser 10 of the present invention, shown in face view. FIG. 1B illustrates an example fabric scent diffuser 10 of the present invention, shown in edge view. Key components illustrated include strap 12, absorbent 16, cover 14, stitching 22, hook and loop A 18, and hook and loop B 20. Strap 12 provides a structural base for attaching absorbent 16, cover 14, hook and loop A 18, and hook and loop B 20. Strap 12 is fabric, which can be chosen for absorbance, non-irritation, durability, beauty, or other properties. Preferably, strap 12 is felted wool fabric. In one preferable example, knitted wool fabric is processed by a felting process which typically uses water and heat to shrink the wool fabric, increasing its density and affecting flexibility and durability. Cover 14 covers and protects absorbent 16 and retains it on strap 12. Cover 14 is fabric, which can be chosen for absorbance, non-irritation, durability, beauty, or other properties. Preferably, cover 14 is felted wool fabric. Cover 14 and strap 12 can comprise the same fabric material, although that is not always required. Preferably, cover 14 is felted wool fabric. After much experimentation with various fabrics and processing, the inventor discovered that felted wool provides an advantageous combination of functional, durability, and aesthetics. In particular, the inventor tried many other fabrics which did not have the durability of felted wool when used in a fabric scent diffuser.

Absorbent 16 is chosen for absorbance, non-irritation, or other properties. Absorbent 16 serves as a reservoir for scent oil or solution 340 (see FIG. 8) so that it can give off scent vapors. Preferably, cotton is used for absorbent 16. The inventor discovered that clean or sterile "cotton ball" material is a good absorbent.

In use, scent oil or solution 340 is applied to fabric scent diffuser 10. By scent oil or solution, we mean any of a variety of oil-based or water-based or other fluid containing active scent or chemical which is desired to deliver by fabric scent diffuser 10. Such scent oil or solution can include room fresheners, bug repellents, fragrances, calming vapors, or other beneficial substances, and can provide pleasing or calming effects, encourage behavior, repel insects or animals, discourage behavior, provide aromatherapy, and so forth. By scent, we mean any vapors or air-transmitted particles or molecules from the scent oil or solution, such as vapors of essential oils, hormones, pheromones, insect repellents, and so forth.

Hook and loop A 18, and hook and loop B 20, are mating components of hook and loop fasteners. Such hook and loop fasteners can comprise those sold under the trade name Velcro®, or other similar fasteners.

Stitching 22 provides attachment of cover 14 to strap 12, thereby holding absorbent 16 in place also. Stitching 22 can comprise one or more filaments, such as a thread, which can be applied by hand or by machine. Stitching 22 can comprise wool or polyester thread, for example. Stitching 22 can pass through cover 14 and strap 12, forming a pocket for absorbent 16, for example. Alternatively, stitching 22 can pass through cover 14 and absorbent 16 and strap 12. Stitching 22 can also be applied to provide attachment of hook and loop A 18, and hook and loop B 20 to strap 12. Alternatively, hook and loop A 18, and hook and loop B 20 can be attached to strap 12 by adhesive or other means.

Figure 2:
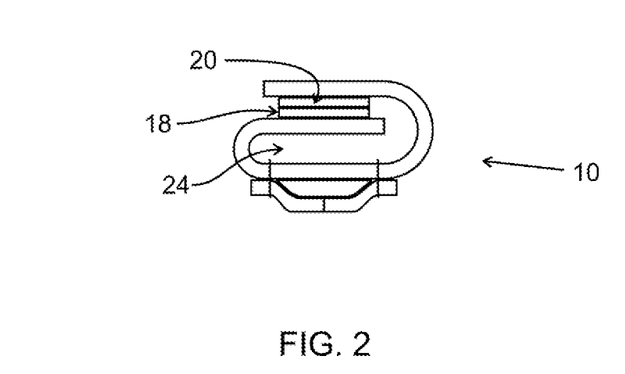
FIG. 2 illustrates the fabric scent diffuser of FIG. 1A with the fabric scent diffuser wrapped around so that the two hook and loop fastener patches are in contact with each other.
Figure 3:
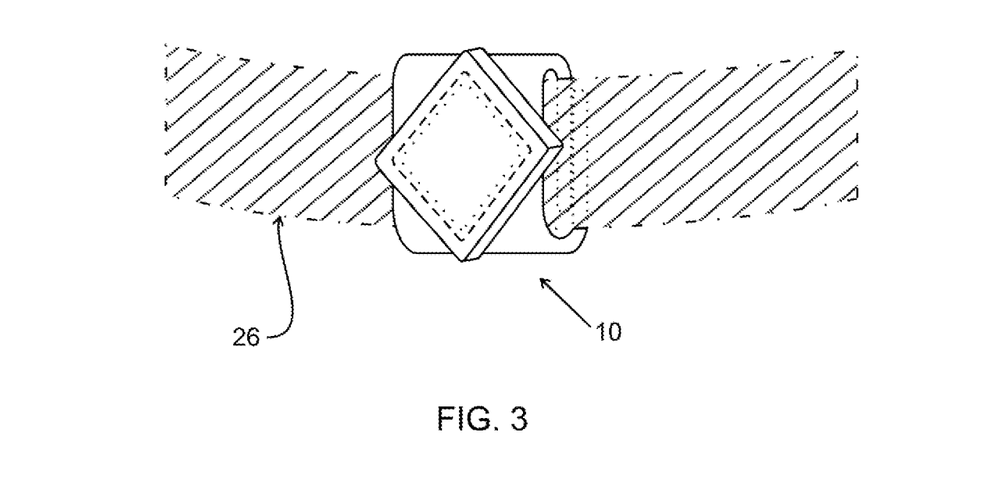
FIG. 3 illustrates the fabric scent diffuser of FIG. 1A with the fabric scent diffuser retained on an example pet collar.
Figure 4A:
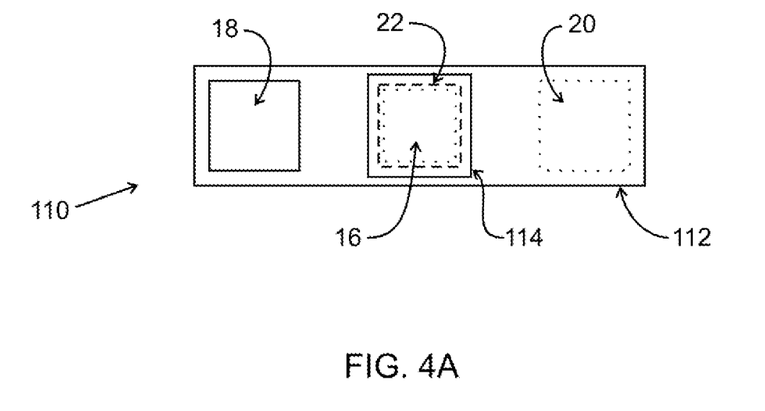
FIGS. 4A-B are similar to a FIG. 1A-B but illustrates a different example fabric scent diffuser, according to the present invention.
Figure 4B:
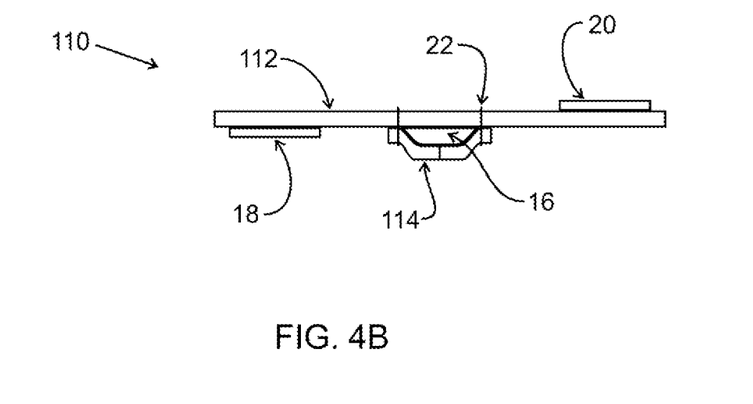
Figure 5:
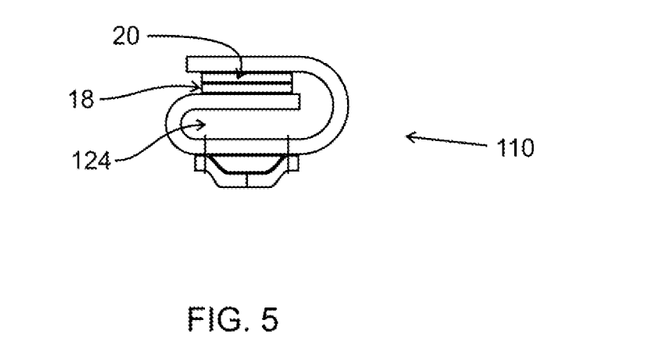
FIG. 5 illustrates the fabric scent diffuser of FIG. 4A with the fabric scent diffuser wrapped around so that the two hook and loop fastener patches are in contact with each other.

FIG. 2 illustrates the fabric scent diffuser 10 of FIG. 1A wrapped around so that hook and loop A 18, and hook and loop B 20 are in contact with each other. Hook and loop A 18, and hook and loop B 20, are chosen to be sufficiently strong so as to remain fastened under the considerable stress as would typically be applied by an animal rubbing, scratching at, biting at, or playing with fabric scent diffuser 10 when attached to a pet collar by hook and loop A 18, and hook and loop B 20 as illustrated in FIG. 3, for example. The positions of hook and loop A 18 and hook and loop B 20 can be reversed, as long as one of them is on each side of strap 12, and near each end of strap 12.

FIG. 3 illustrates the fabric scent diffuser 10 of FIG. 1A wrapped around an example pet collar 26 (not part of fabric scent diffuser 10). Pet collar 26 can be a typical collar placed around the neck of an animal, or can be a strap of a harness or halter, leash, tie-down, or other similar equipment. Fabric scent diffuser 10 can be attached to other equipment if desired, such as a pet cage, as long as the equipment has a place where fabric scent diffuser 10 can be passed around and secured to a portion of the equipment.

FIGS. 4A, 4B, 5, and 6 illustrate another example fabric scent diffuser 110 of the present invention, similar to that shown in FIGS. 1-3. Key components illustrated include strap 112, absorbent 16, cover 114, stitching 22, hook and loop A 18, and hook and loop B 20. In this case, absorbent 16 and cover 114 are aligned differently than absorbent 16 and cover 14 of FIGS. 1-3. This different alignment can be useful when fabric scent diffuser 110 is to be attached to a narrower pet collar 126, for example, and provides a corresponding narrower passage for pet collar 124.

Similar fabric scent diffusers can be made by incorporating additional layer(s) of absorbent 16 or additional layer(s) of cover 14. For example, a "pillow" can be made of two layers of cover 14, filled with absorbent 16 which is located between the two layers of cover 14. This completed "pillow" can be attached to strap 12, forming a structure quite similar to those of FIGS. 1-6, but with an additional layer of cover 14. A similar modification can be incorporated into fabric scent diffuser 110 or other fabric scent diffusers of the present invention.

Figure 6:
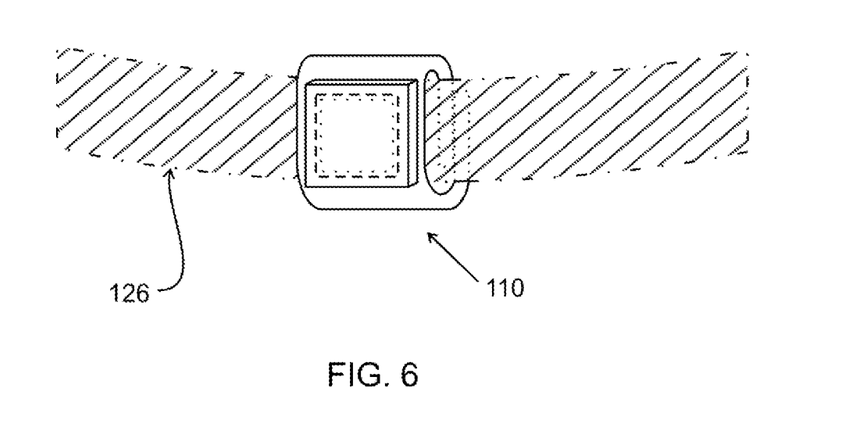
FIG. 6 illustrates the fabric scent diffuser of FIG. 4A with the fabric scent diffuser retained on an example pet collar.
Figure 7A:
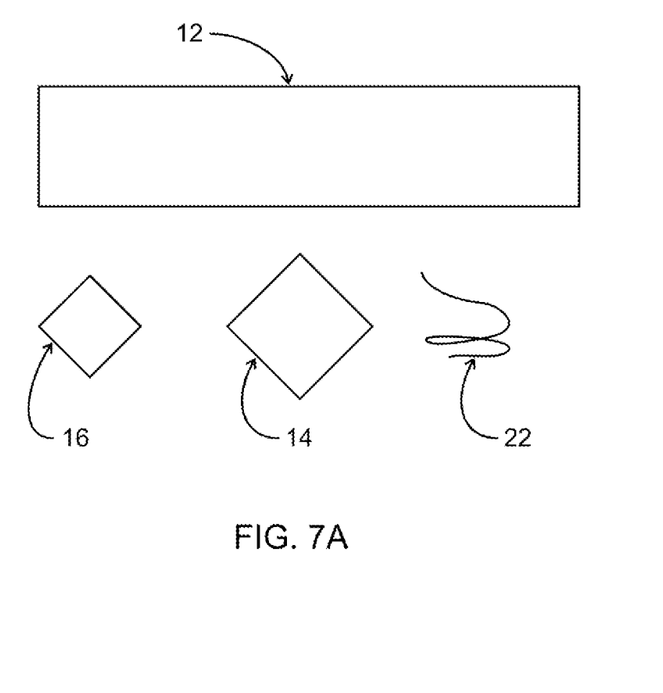
FIGS. 7A-7D illustrates various components of the fabric scent diffuser of FIG. 1A and shows steps of fabricating the fabric scent diffuser.
Figure 7B:
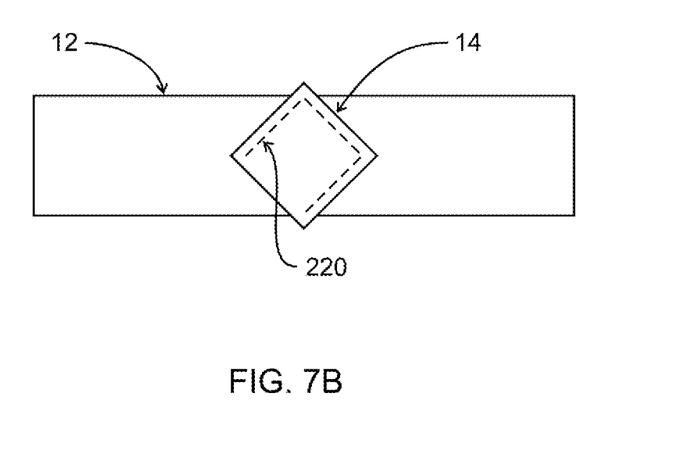
Figure 7C:
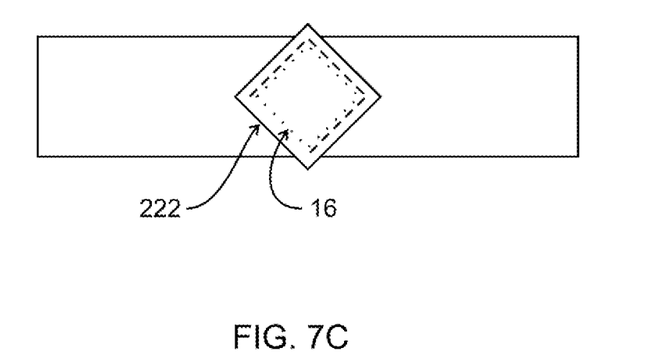
Figure 7D:
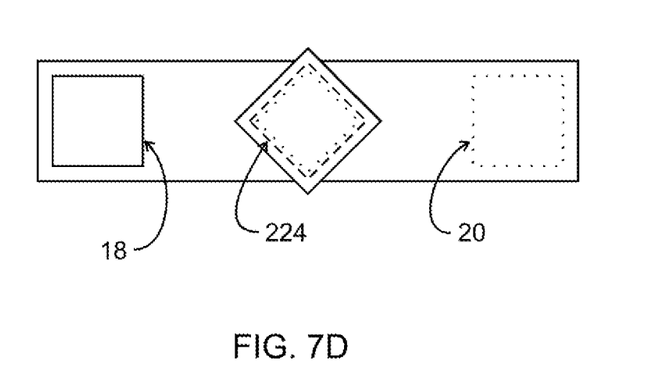

A plurality of fabric scent diffusers can be attached to a pet collar, or other pet equipment in a manner similar to that shown on FIGS. 3 and 6.

FIGS. 7A-D illustrate steps in fabrication of a fabric scent diffuser according to the present invention. First, strap 12, absorbent 16, cover 14, and stitching 22 are provided. Next, cover 14 is attached to strap 12 by hand or machine stitching around most of cover 14 (such as 3 sides of a 4 sided cover, indicated as stitched portion of cover 220) forming a pocket with an open access portion (indicated as non-stitched portion of cover 222). Then, absorbent 16 is stuffed into the pocket, and additional stitching 224 is applied to close the pocket and retain absorbent 16. Attachment of hook and loop A 18, and hook and loop B 20 are then attached by stitching or by adhesive attachment as described above. A similar approach can be used with an additional layer of cover 14, as descried above, by first forming a pillow by stitching two layers of cover 14 with absorbent 16 between the layers of cover 14, and then stitching the pillow to strap 12.

Figure 8:
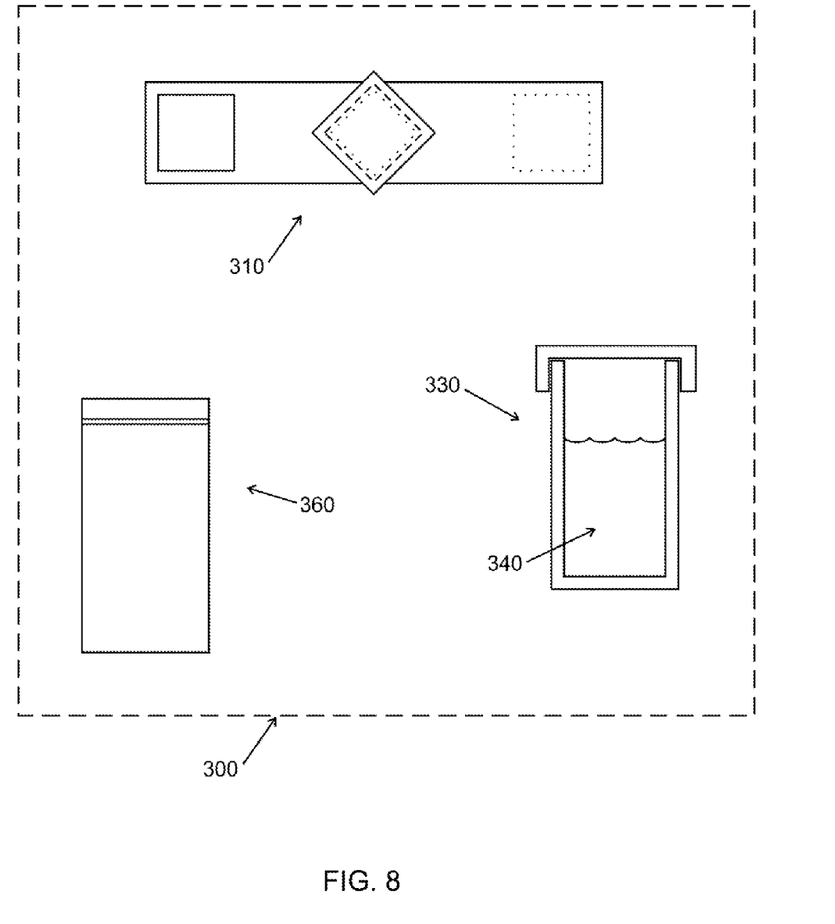
FIG. 8 illustrates a kit including a fabric scent diffuser such as that of FIG. 1A, a container of scent oil or solution, and a storage container.

FIG. 8 illustrates fabric scent diffuser kit 300 including fabric scent diffuser 310, sealable scent oil container 330, scent oil or solution 340, and sealable scent diffuser storage container 360 to protect fabric scent diffuser 310 and slow the drying out of scent oil or solution 340 which has been applied to fabric scent diffuser 310. Optionally, the kit can further include an applicator such as an eyedropper, or a tip for the sealable scent oil container 330, to facilitate controlled application of scent oil or solution 340 to fabric scent diffuser 310. Optionally, the kit can include a plurality of scent oil containers 330, instructions for use, or a kit case to store the scent oil container(s) 330 (containing scent oils or solutions 340) and the sealable scent diffuser storage container 360 (with fabric scent diffuser 310 inside).

Cover (14, 114, etc.) is illustrated herein as square or diamond shaped. While these are shapes used by the inventor for covers, other shapes can also be used. For example, triangular, rectangular, rhomboid, or other polygonal shapes can be used, round or oval shapes can be used, or arbitrary curves or combination shapes, as long as they are chosen to fit with the appropriate strap (12, 112, etc.) and can be effectively stitched to cover and secure absorbent 16. Cover 14 can even be shaped similarly to strap 12; in this case fabric scent diffuser 10 could be two layers of fabric stitched together with absorbent 16 captured between them, and hook and loop A 18 and hook and loop B 20 attached near the ends. Similarly, strap (12, 112, etc.) is illustrated herein as rectangular, but could be tapered, curved, or have combination of shapes, as long as the shapes are chosen to fit with cover (14, 114, etc.) and allow effective stitching to cover and secure absorbent 16. The pillow structure and fabrication approach described above can easily allow alternative shapes such as these. Further, a more three-dimensional shape can be utilized, where additional absorbent material is stuffed into a pocket or pillow, or stitching is used retain a thicker portion or to form quilted or other shape.

The fabric of the present fabric scent diffuser is chosen for superior wicking and diffusion, fabrication characteristics, durability, and aesthetics. Various fabrics could be utilized, but the best fabric so far discovered for use in the present fabric scent diffuser is felted knit wool fabric. The felting process typically uses water, heat, and agitation to densify the knitted wool. During the felting process, small scales on the wool deform, changing the flexibility of the fabric and locking the structure together more firmly, while the fabric generally shrinks in overall size. The specific knitted wool structure which was discovered to be most useful for the present fabric scent diffuser, is a "four-color", or technically four-strand (since color primarily affects the appearance rather than the resulting structure) double-bed jacquard knit material. When felted, this material provides a dense yet flexible, beautiful but durable, material for the present fabric scent diffuser. In addition, this material resists fraying at the edges, so that it eliminates the need to stitch or otherwise reinforce the cut edges of the fabric. Further, the resulting fabric structure provides effective wicking of scent oil or solution, and diffusion of scent when used in the present fabric scent diffuser.

The structure of the present fabric scent diffuser, being primarily layers of fabric, lays down and conforms closely to the animal's body and to the collar. This conformity is useful in reducing the "catching" of the fabric scent diffuser, so that the fabric scent diffuser is less likely to be dislodged by the animal scratching or other activity. The structure also provides flexibility and "give", which enhances the comfort and aesthetic qualities of the fabric scent diffuser.

Fabric scent diffusers of the present invention provide many advantages over prior approaches, including the following. The area for diffusion is greater than in prior approaches with a small access hole. The fabric, and especially the preferred felted four-strand double-bed jacquard knit wool fabric as described above, provides improved wicking and diffusion of scent. The fabric, and especially the preferred felted four-strand double-bed jacquard knit wool fabric as described above, provides enhanced durability and resistance to fraying. The structure of the present fabric scent diffuser, being primarily of fabric, has no sharp edges, and will not fracture during abuse, and is thus safer for an animal. The structure of the present fabric scent diffuser, being primarily layers of fabric, will lay more compactly and closely against the collar and the animal and conforms and integrates better with the animal configuration and curves and shapes of the animal's body.

Various modifications can be made to the present invention without departing from the apparent scope thereof.

PARTS LIST 10 fabric scent diffuser
12 strap
14 cover
16 absorbent
18 hook and loop A
20 hook and loop B
22 stitching
24 passage for pet collar
26 pet collar
110 fabric scent diffuser
112 strap
114 cover
124 passage for pet collar
126 pet collar
220 stitched portion of cover
222 non-stitched portion of cover
224 stitching (final portion)
300 fabric scent diffuser kit
310 fabric scent diffuser
330 scent oil container
340 scent oil or solution
360 scent diffuser storage container It is claimed:

1. A pet collar, comprising:
    a pet collar;
    a fabric strap having first and second opposite ends and adapted to be removably attached to said pet collar;
    a fabric cover, having a predetermined geometrical configuration so as to define a perimeter portion having a predetermined geometrical configuration and located atop said fabric strap so as to effectively define a pocket with said fabric strap;
    absorbent material, serving as a reservoir for a scented composition which emits and diffuses scented vapors, disposed within said pocket between said fabric strap and said fabric cover and to define with said fabric strap and said fabric cover a scent diffuser;
    stitching defined around the entire extent of said perimeter portion of said fabric cover for fixedly securing said fabric cover to said fabric strap and for fixedly retaining said absorbent material within said pocket defined between said fabric strap and said fabric cover; and
    hook and loop fasteners attached to said opposite ends of said fabric strap so as to permit said fabric strap to be removably attached to said pet collar.

2. The pet collar of claim 1, wherein the fabric strap comprises felted wool.

3. The pet collar of claim 1, wherein the fabric cover comprises felted wool.

4. The pet collar of claim 1, wherein the absorbent material comprises cotton.

5. The pet collar of claim 1, wherein the fabric strap comprises felted four-strand double-bed jacquard knit wool.

6. In combination, a pet collar and a kit for providing scent oil for a scent diffuser of the pet collar and a storage container for storing the scent diffuser, comprising:
    a pet collar;
    a fabric strap having first and second opposite ends and adapted to be removably attached to said pet collar;
    a fabric cover, having a predetermined geometrical configuration so as to define a perimeter portion having a predetermined geometrical configuration and located atop said fabric strap so as to effectively define a pocket with said fabric strap;
    absorbent material, serving as a reservoir for a scented composition which emits and diffuses scented vapors, disposed within said pocket between said fabric strap and said fabric cover and to define with said fabric strap and said fabric cover a scent diffuser;
    stitching defined around the entire extent of said perimeter portion of said fabric cover for fixedly securing said fabric cover to said fabric strap and for fixedly retaining said absorbent material within said pocket defined between said fabric strap and said fabric cover;
    hook and loop fasteners attached to said opposite ends of said fabric strap so as to permit said fabric strap to be removably attached to said pet collar;
    a scent oil container for containing scent oil to be applied to said absorbent material of said scent diffuser; and
    a storage container for containing said scent diffuser so as to protect said absorbent material of said scent diffuser from drying out.

7. The combination of claim 6, further comprising:
    a case to store said scent oil container, said scent diffuser, and said scent diffuser storage container.

8. The pet collar as set forth in claim 2, wherein:
    said felted wool fabric strap comprises knitted wool fabric.

9. The pet collar as set forth in claim 3, wherein:
    said felted wool fabric cover comprises knitted wool fabric.

10. The combination of claim 6, wherein:
    said fabric strap comprises felted wool.

11. The combination of claim 6, wherein:
    said fabric cover comprises felted wool.

12. The combination as set forth in claim 10, wherein:
    said felted wool fabric strap comprises knitted wool fabric.

13. The combination as set forth in claim 11, wherein:
    said felted wool fabric cover comprises knitted wool fabric.

14. The combination as set forth in claim 6, wherein:
    said absorbent material comprises cotton.

15. The combination as set forth in claim 6, wherein:
    said fabric strap comprises felted four-strand double-bed jacquard knit wool.

* * * * *